United States Patent
Behbehani et al.

[11] Patent Number: 6,142,952
[45] Date of Patent: Nov. 7, 2000

[54] METHOD AND APPARATUS FOR DETECTION AND DIAGNOSIS OF AIRWAY OBSTRUCTION DEGREE

[75] Inventors: Khosrow Behbehani, Arlington; John R. Burk, Aledo; Edgar R. Lucas, Fort Worth; Fu-Chung Yen, Arlington, all of Tex.

[73] Assignee: The Board of Regents, The University of Texas System, Austin, Tex.

[21] Appl. No.: 08/959,938

[22] Filed: Oct. 29, 1997

[51] Int. Cl.⁷ ................................................ A61B 5/085
[52] U.S. Cl. ...................... 600/533; 600/532; 600/538; 600/529; 600/484
[58] Field of Search .................. 600/529, 531–535, 600/481, 483, 484

[56] References Cited

U.S. PATENT DOCUMENTS

| | | | |
|---|---|---|---|
| 5,134,995 | 8/1992 | Gruenke et al. | 600/532 |
| 5,318,038 | 6/1994 | Jackson et al. | 600/529 |
| 5,513,648 | 5/1996 | Jackson | 600/529 |
| 5,535,739 | 7/1996 | Rapoport et al. | 600/538 |
| 5,549,106 | 8/1996 | Gruenke et al. | 600/532 |
| 5,704,345 | 1/1998 | Berthon-Jones | 600/529 |

*Primary Examiner*—John P. Leubecker
*Assistant Examiner*—Roy Gibson
*Attorney, Agent, or Firm*—Felsman, Bradley, Vaden, Gunter & Dillon, LLP

[57] ABSTRACT

A pressurized breathable gas, preferably air, is supplied to the patient's airways with an interface including a mask and a flexible hose. A selected oscillation component or forced probing signal is applied or superposed on the pressurized breathable gas, preferably with a loudspeaker coupled to a frequency generator. Pressure and flow of the breathable gas in the interface are measured or sampled, preferably using pressure transducers and a pneumotachometer coupled to a personal computer, to obtain pressure and flow data characteristic of the patient's airway. The pressure and flow data are converted to the frequency domain using Fourier transform or cross-power spectrum techniques in the personal computer. A function of the processed pressure and flow data is obtained to determine an index of airway impedance or degree of airway obstruction.

16 Claims, 5 Drawing Sheets

METHOD AND APPARATUS FOR DETECTION AND DIAGNOSIS OF AIRWAY OBSTRUCTION DEGREE

BACKGROUND OF THE INVENTION

1. Field of the Invention

The present invention relates generally to methods and apparatus for the detection of the degree of airway obstruction of a human patient, which can be useful in the diagnosis and treatment of sleep disorder breathing and other respiratory and pulmonary difficulties.

2. Background Information

Disorders of excessive sleepiness present particular health-care concerns. Patients suffering from these disorders experience drowsiness and the need or desire to take naps during the day, and such patients present a history of divorces, employment problems, and automotive accidents.

Among the most common types of sleep disorder breathing is sleep apnea, in which patients experience a partial or complete interruption of air flowing into the lungs for periods exceeding ten seconds. Between 1% and 15% of the population is believed to suffer from this condition. Sleep apnea can cause repeated disruption or even cessation of rapid eye movement (REM) sleep, which can cause irritability and a reduction in the ability to memorize information.

There are three recognized types of sleep apnea. Central sleep apnea is characterized by the suspension of all respiratory movement and is generally believed to be neurological in origin. Obstructive sleep apnea is characterized by the collapse of the upper airways during sleep. The third type of sleep apnea is a combination of central and obstructive sleep apnea and is known as mixed apnea.

Obstructive sleep apnea appears to be the most common form of sleep apnea and occurs when the upper respiratory airway of the patient collapses because the tonal activity of the pharyngeal smooth muscle fails to maintain the patency of the airway. Although sporadic and brief airway collapses or obstructive events are not uncommon in the normal adult population, it is considered pathological when obstructive apnea episodes last more than ten seconds and occur over seven-to-ten times per hour.

A symptom indicative of the onset of obstructive sleep apnea is pharyngeal wall vibration, commonly known as snoring when audible. Early detection of pharyngeal wall vibration, and prophylactic treatment of the condition, can lead to successful treatment of obstructive sleep apnea. Surgical treatments of obstructive sleep apnea are successful when anatomical abnormalities appear to be the principal cause of obstructive sleep apnea. Non-surgical treatments are successful as well.

One successful non-surgical treatment method is the use of continuous positive airway pressure (CPAP) apparatus. CPAP apparatus administers air or respiratory gas to the patient's airways at a slightly positive pressure level (5 to 20 cmH$_2$O), which maintains the patency of the respiratory airways. The pressure exerted by CPAP apparatus is believed to act as a pneumatic splint for the upper airway. The low-level pressure of the CPAP apparatus is selected after study of the patient in a sleep laboratory. The selected pressure from the sleep study is referred to as "prescribed" CPAP pressure. Although CPAP apparatus is an effective treatment in 75% of treated patients, the positive airway pressure delivered throughout sleep can cause patient discomfort, including airway pain and dehydration.

All treatments of sleep disorder breathing depend, to one degree or another, upon accurate diagnosis of the degree and type of airway obstruction. The foregoing methods and apparatus detect airway obstruction or other precursors to apneic events, but in a relative sense only (relative to previous inhalations and exhalations). While they are useful therapeutic tools, their ability to detect and diagnose the degree of airway obstruction in an abstract or absolute sense, as a diagnostic tool, is limited. Indeed, most provide no easy way of communicating this information directly to the treating physician or therapist.

Attempts have been made in the past to estimate the degree of obstruction of the airway of a patient's respiratory system. One technique is known as the forced oscillation technique (FOT). In this technique, an audio loudspeaker is coupled to the airway via a rigid mounting. A probing signal is generated by the loudspeaker and propagated into the airway. Respiratory impedance then is calculated from analysis of pressure and flow signals measured at the airway opening. Due to the sensitivity of the instruments used, the patient is typically awake, in an upright sitting position, and may not breathe during measurement.

Another technique for estimating airway obstruction degree or impedance is known as the airway resistance technique (ART). In this technique, a pressure pulse generated by a loudspeaker is passed to the airway through a straight, rigid tube. By analyzing the acoustic characteristics of the echo (reflected and refracted sound wave), the changes in the effective cross-section or diameter of the airway can be measured.

Both of these techniques are minimally invasive in that they do not require insertion of nasal, pulmonary, or interpleural catheters and the like. However, both methods restrict patient movement through the use of rigid mountings and must be undertaken under fairly controlled circumstances, such as seated and without the patient breathing (in the case of FOT). Many types of breathing disorders, e.g. sleep apnea, occur during sleep or other conditions perhaps not easily reproduced in the laboratory.

A need exists, therefore, for methods and apparatus for the detection and diagnosis of the degree and character of the airway obstruction of a patient that are minimally invasive and permit diagnosis during normal patient activity, preferably sleep.

SUMMARY OF THE INVENTION

It is a general object of the present invention to provide a method and apparatus for the detection and diagnosis of the degree and character of the airway obstruction of a patient.

This and other objects of the present invention are achieved by supplying a pressurized breathable gas, preferably air, to the patient's airways with an interface comprising a mask and a flexible hose. A selected oscillation component or forced probing signal is applied or superposed on the pressurized breathable gas, preferably with a loudspeaker coupled to a frequency generator. Pressure and flow of the breathable gas in the interface are measured or sampled, preferably using pressure transducers and a pneumotachometer coupled to a personal computer, to obtain pressure and flow data characteristic of the patient's airway. The pressure and flow data are converted to the frequency domain using Fourier transform or cross-power spectrum techniques in the personal computer. A function of the processed pressure and flow data is obtained to determine an index of airway impedance or degree of airway obstruction.

According to the preferred embodiment of the present invention, the measured pressure and flow data are processed to eliminate data having indicia of unreliability after converting it to the frequency domain.

According to the preferred embodiment of the present invention, the pressure data is divided by the corresponding flow data to obtain an airway impedance or degree of airway obstruction value and a mean impedance or degree of airway obstruction is determined from the airway impedance or degree of airway obstruction values.

Other objects, features, and advantages of the present invention will become apparent with reference to the drawings and corresponding detailed description, which follow.

DETAILED DESCRIPTION OF THE INVENTION

Figure 1:
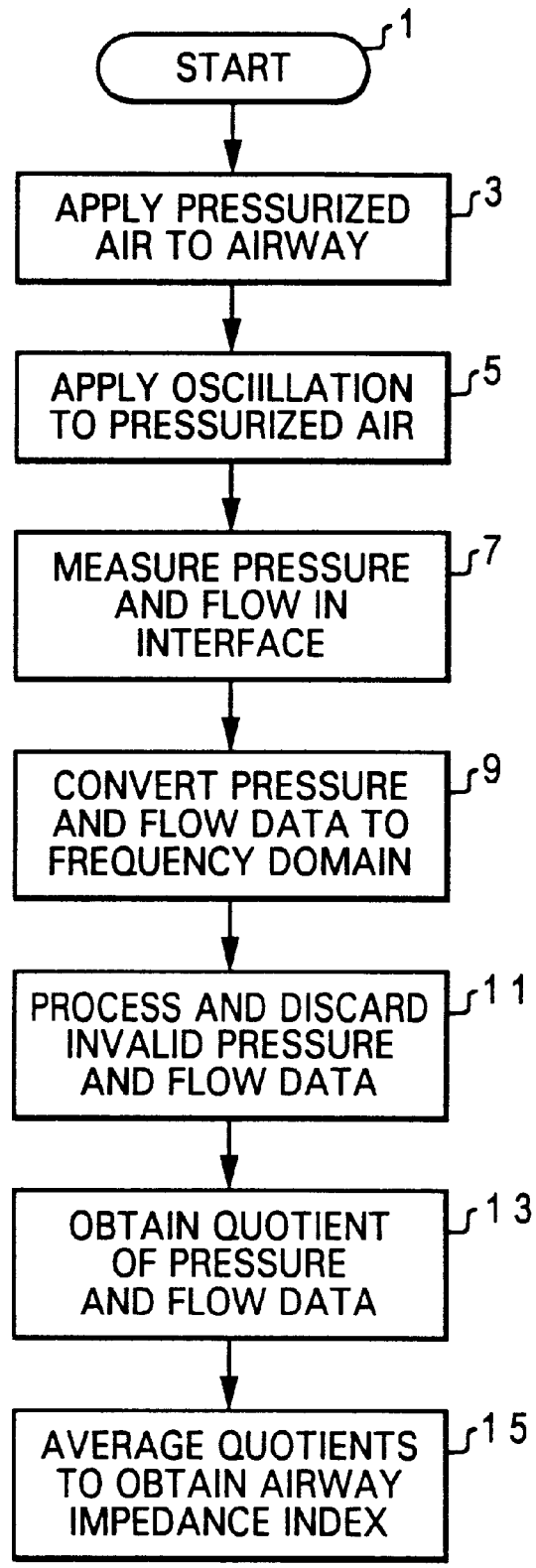
FIG. 1 is a high-level flow chart depicting the implementation of the method according to the present invention.

Referring now to the Figures, and in particular to FIG. 1, a high-level flow chart depicting the implementation of the method according to the present invention is shown. At the step represented by block 1, an interface is coupled to the respiratory airway of a patient. The interface includes sensors or transducers for measuring pressure and flow in the interface. As represented at block 3, a source of pressurized breathable gas is activated and the gas, preferably ambient air, is provided to the patient's airways through the interface.

Simultaneously or near-simultaneously, a selected oscillation component or forced probing signal is delivered or applied to the patient's airways along with the pressurized air, as represented by block 5. A personal computer and associated sampling equipment are coupled to pressure and flow sensors or transducers in the interface and are initiated to begin data sampling.

As represented by block 7, measured pressure and flow data measured are collected or sampled. This data is converted to digital form and a Fourier transform is performed to convert the measured pressure and flow data to the frequency domain, as represented by block 9.

Because of noise in the system and noise generated by patient breathing, the converted pressure and flow data ensembles must be processed and noisy or unreliable data ensembles discarded, as represented by block 11.

After the invalid data is discarded, the a function, preferably the quotient, of the pressure and flow spectra is obtained, as represented at block 13. This yields a measure of the airway impedance or degree of obstruction. Finally, as represented at block 15, an average or index of respiratory impedance or obstruction, $I_z$, is obtained.

Figure 2:
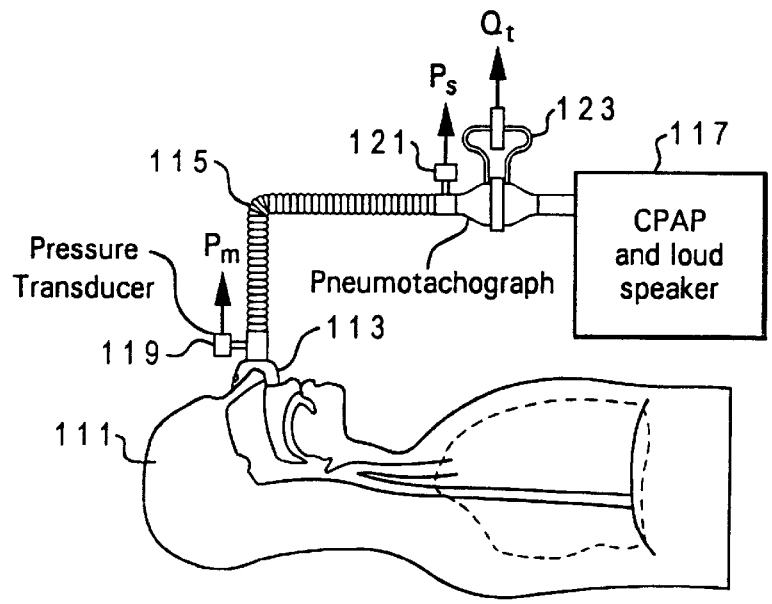
FIG. 2 is a schematic depiction of the apparatus for practicing the method according to the present invention.

FIG. 2 is a schematic depiction of the apparatus for practicing the method according to the present invention is depicted. A patient 111 is fitted with an interface over his or her breathing passages, preferably the nose or nasal passages. According to the preferred embodiment of the present invention, the interface comprises a mask 113 (Reusable Contour Nasal Mask, Respironics, Murrysville, Pa.), which is connected by a flexible hose 115 to a supply of pressurized breathable gas 117 or ambient air. According to the preferred embodiment of the present invention, the supply of pressurized breathable gas is a CPAP device (BiPAP S-D, Respironics, Murrysville, Pa.), which is provided with a blower for delivering air at elevated pressures (up to 20 cmH$_2$O) through hose 115 and mask 113 to the airways of patient 111. As described in connection with FIG. 5, an audio loudspeaker preferably is also incorporated or associated with the CPAP blower.

A pressure transducer 119 (163PC01D48, MicroSwitch, Freeport, Ill.) is provided where mask 113 connects to hose 115. Another, similar pressure transducer 121 is provided near or at the juncture of hose 115 and air source 117. Pressure transducers 119, 121 measure total pressure of the breathable gas in or at mask ($P_s$) 113 and at or near source of pressurized gas ($P_m$) 117. A Fleisch pneumotachometer 123 is provided between source of pressurized air 117 and hose 115 for measuring the flow rate of air ($Q_t$) provided by supply 117.

Figure 3:
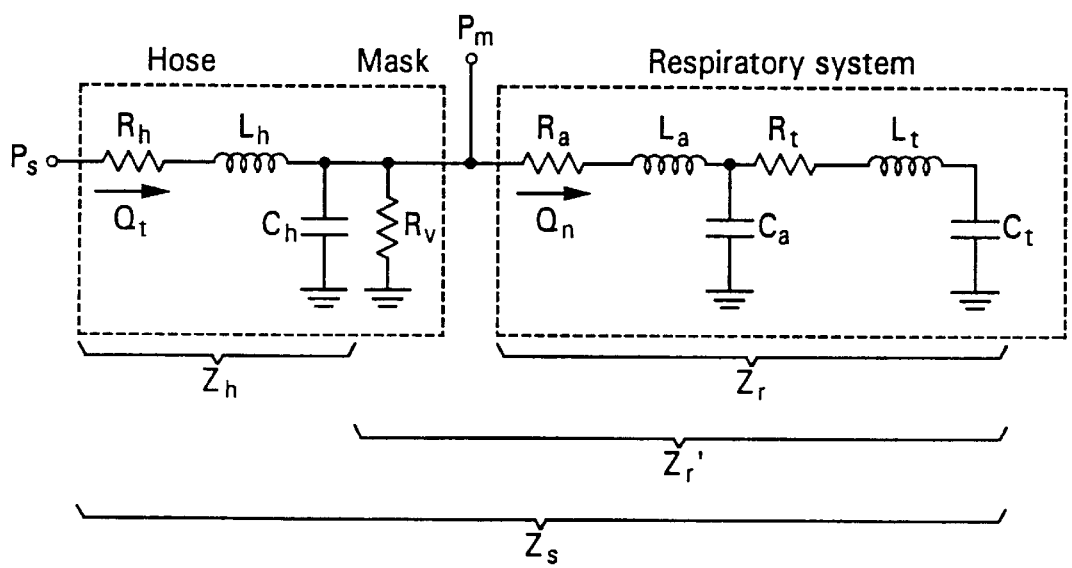
FIG. 3 is an electrical schematic representation of the system of FIG. 2.

FIG. 3 is an electrical schematic representation of the system of FIG. 2. Beginning at the left of the diagram, $P_s$ represents the supplied pressure of the breathable gas or ambient air. The value $R_h$ is the resistance loss through hose 115, $L_h$ is the inertance of the hose, and $C_h$ is the compliance or resilience of the hose. The value $R_v$ represents the resistance of the venting port located on the mask. Because mask 113 is essentially rigid, its compliance is ignored. These variables can be combined or lumped and considered to obtain the impedance of the hose $Z_h$. The value $P_m$ represents the pressure measured at mask 113 by transducer 119.

The flow rate after pressurized air has passed through the impedance $Z_h$ of hose 115 and is applied to the airways or respiratory system of patient 111 is represented by $Q_r$. The resistance, inertance, and compliance of the respiratory airway of patient 111 are represented by the values $R_a$, $L_a$, and $C_a$, respectively. The resistance, inertance, and capacitance of the lungs and thoracic cage are presented by $R_l$, $L_l$, and $C_l$, respectively. The combined impedance of the patient's respiratory system and the mask vent resistance $R_v$ is thus represented by $Z_r'$. The value $Z_r$ represents the impedance of the respiratory system as a whole and is the quantity of interest in method of the present invention.

The values of $R_h$, $L_h$, and $C_h$ were determined experimentally to be relatively small at low frequencies (<100 Hz). Thus, these elements can be ignored and the electrical analogous circuit of FIG. 3 can be simplified to the electrical circuit schematic of FIG. 4, where $Q_t$ is the flow rate measured through pneumotachometer 123, $P_m$ is the pressure measured at mask 117, and $Q_v$ and $R_v$ are the flow and resistance through the venting port of mask 113, respectively. The values $Z_r'$ and $Z_r$ are the same as in FIG. 3.

Figure 5:
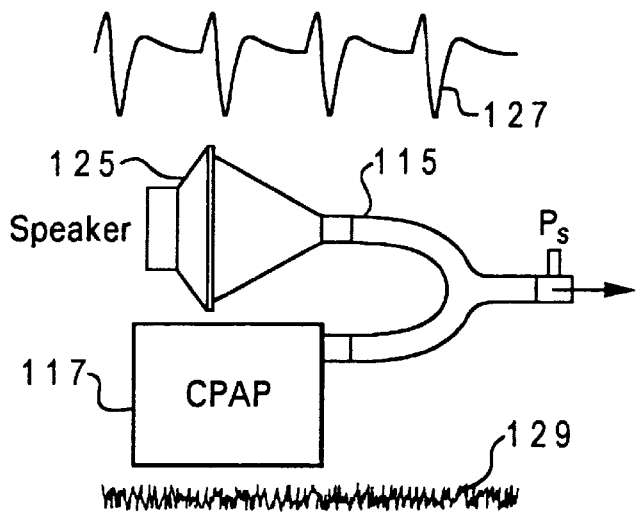
FIG. 5 is a schematic illustration of the superposition or application of a multi-frequency oscillation signal to the pressurized air supplied from the blower.

FIG. 5 is a schematic illustration of the superposition or application of a multi-frequency oscillation signal to the pressurized air supplied from the blower or CPAP device. As is illustrated, an eight-inch loudspeaker (Realistic 40-11348, Radio Shack) 125 and CPAP blower 117 are coupled to hose 115 to deliver both pressurized ambient air and the multi-frequency oscillation. A sample trace of the multi-frequency oscillation is indicated at 127. A sample trace of the turbulent noise resulting from the action of CPAP blower 117 is illustrated at 129. Multi-frequency oscillation 127 depicted in FIG. 5 is the result of a 4 Hz sawtooth wave from a function generator being pre-amplified and propagated from loudspeaker 125.

Figure 6:
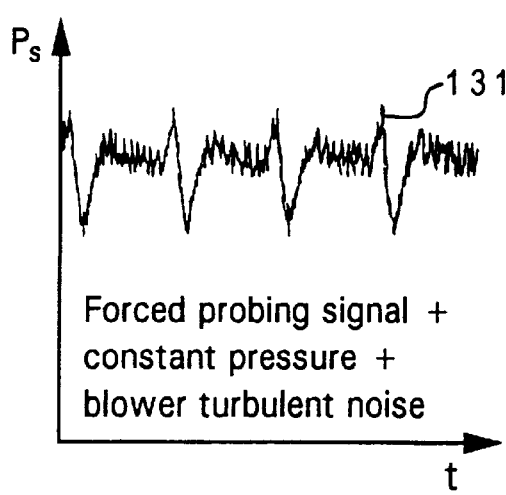
FIG. 6 is a graph, in the time domain, of the pressure wave or signal resulting from the superposition of the multi-frequency oscillation upon the pressurized air from the blower.

FIG. 6 is a graph, in the time domain, of $P_s$ (supply pressure), or the pressure wave 131 resulting from the superposition of the multi-frequency oscillation (127 in FIG. 5) upon the pressurized air from the blower (117 in FIG. 5). The result is a composite signal or wave 131 that bears characteristics of both of the component signals. The relatively high-amplitude, periodic portion of the signal 131 corresponds to the oscillation (127 in FIG. 5) applied or superposed by the speaker (125 in FIG. 5) on the pressure supplied from the blower and noise (129 in FIG. 5) generated by the blower (117 in FIG. 3). This component is referred to as a "forced probing signal." The low-amplitude, high-frequency portion of the signal corresponds to turbulent noise generated by the blower. In selecting the forced probing signal or oscillation, its frequency should be less than about 20 Hz to avoid being audible to patient 111 during sleep and should have a peak-to-peak amplitude less than about 0.5 $cmH_2O$ to avoid vibration being detected by the patient.

Although superposition of the forced probing signal using a loudspeaker is the preferred embodiment, other methods could be used as well. For example, the blower portion of CPAP device 117 could be modified (by impeller blade imbalance, an intermittent valve, and the like) to deliver a characteristic frequency for use as a forced probing signal.

Figure 7:
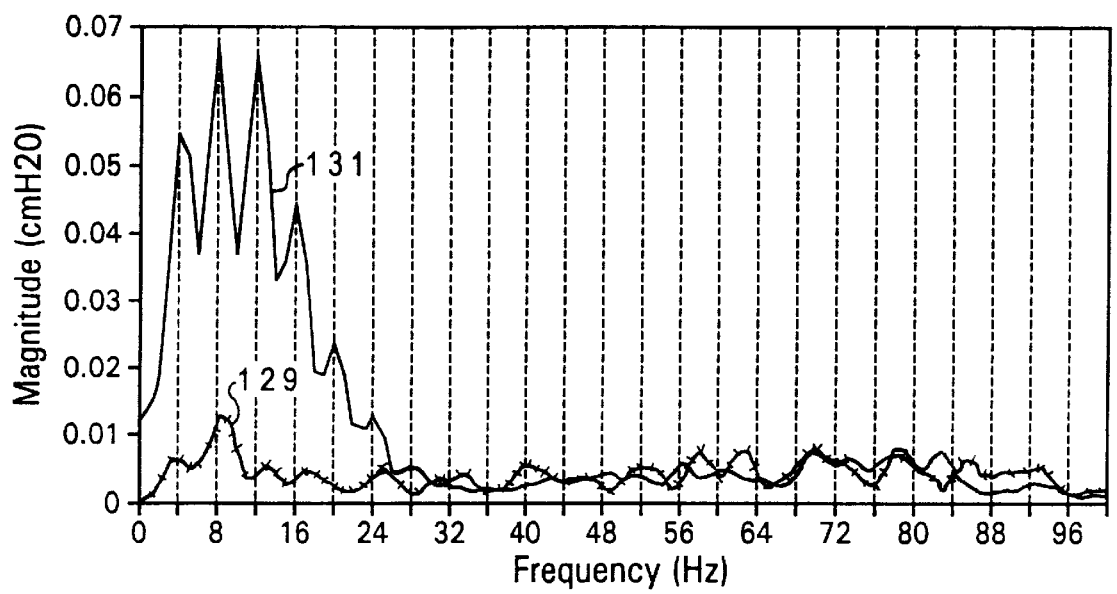
FIG. 7 is a graph of the frequency spectra of waveforms with and without the multi-frequency oscillation.

FIG. 7 is a graph of the frequency spectra of waveform 131 from FIG. 6 and waveform 129 from FIG. 5. As can be seen, there are distinct peaks in the frequency spectra from about 4 to 24 hz, which correspond to the forced probing signal frequencies superposed on the turbulent noise and constant pressure from the blower signal 129. Thus, by converting measured data to the frequency domain as in FIG. 7, the spectral components of the signals can be discerned rather easily. According to the preferred embodiment of the present invention, data from the frequency domain, similar to that shown in FIG. 7 is used for calculation of the airway obstruction degree or impedance.

Figure 4:
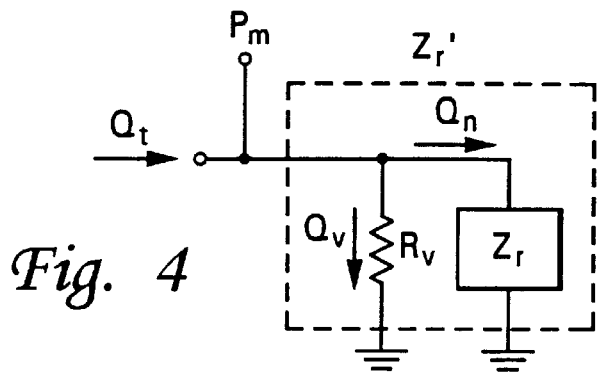
FIG. 4 is a simplification of the schematic of FIG. 3.

According to the simplified electrical model of FIG. 4, the respiratory impedance or degree of obstruction $Z_r$ can be estimated by first calculating the combined impedance $Z_r'$ using the Fourier Transform Ratio Method:

$$Z_r'(\omega) = \frac{S_{P_m}(\omega)}{S_{Q_t}(\omega)} \quad (1)$$

Where $S_{Pm}(\omega)$ is the Fourier transform of $P_m(t)$, and $S_{Qt}(\omega)$ is the Fourier transform of $Q_t(t)$. As an alternative to the Fourier Transform Ratio method (Equation (1)), the Cross-Power Spectrum method may be used to determine $Z_r'$:

$$Z_r' = \frac{G_{PmPm}(\omega)}{G_{QtPm}(\omega)} \quad (2)$$

Where $G_{PmPm}(\omega)$ is the cross-power spectrum of the mask pressure signal ($P_m$) and $G_{QtPm}(\omega)$ is the cross-power spectrum of the airflow ($Q_t$) and mask pressure ($P_m$). The Cross-Power Spectrum method uses more computational power and takes nearly 10 times as long as the Fourier Transform Ratio method, but is more accurate, especially when the system is noisy and/or there is a low signal-to-noise ratio between the forced probing signal and the system noise.

The impedance of the respiratory system $Z_r$ is obtained by the following relation:

$$Z_r = \frac{R_v \cdot Z_r'}{R_v - Z_r'} \quad (3)$$

Where $R_v$ is the vent resistance of the mask and is determined by dividing the baseline pressure supplied by the blower by the flow rate from the mask venting port. Given that baseline blower pressure is known, venting occurs to the atmosphere, and mask pressure is known ($P_m$), the flow rate through the venting port can be calculated and the value of $R_v$ calculated.

Thus, by applying or superposing a forced probing signal 127 or oscillation upon the constant pressure and noise signal 129 from blower 117, an airway impedance value indicative of the degree of airway obstruction at a given frequency may be calculated using equations (1) and (2). Use of the Fourier transforms or cross-power spectra of measured pressure and flow data to calculate the impedance requires that the time-domain data measured by pressure transducers 119, 121 and pneumotachometer 123 be converted to the frequency domain.

Thus, at least the outputs of pressure transducers 119, 121 and pneumotachometer 123 are input to a personal computer (Intel® 80486 DX133 or equivalent processor) with a data-sampling and processing card or feature or other means of obtaining the frequency spectrum of the pressure and flow signals. The measured pressure and flow data are converted to digital data using a conventional analog-to-digital converter (DASH16, 12-bit, Keithley/Metrabyte, Taunton, Mass.) and then are converted to the frequency domain using Fourier transform analysis. Prior to conversion to digital data, all data is filtered by analog low-pass filters (2nd order active filter) to remove high-frequency noise in the $Q_t$, $P_s$, and $P_m$ signals and to prevent aliasing while signals are sampled by the analog-to-digital converter. The cut-off frequency of the pre-sampling filters for the $Q_t$, $P_s$, and $P_m$ signals are 150, 170, and 170 Hz respectively. According to the preferred embodiment of the present invention, all data is sampled at 1024 Hz, but other sampling rates may be used. According to the preferred embodiment of the present invention, the 1024 Hz rate is selected because a 0.25 second sample corresponding to one cycle of the forced probing signal (4 Hz) yields 256 data points.

Template/MSE Data Processing

Figure 8:
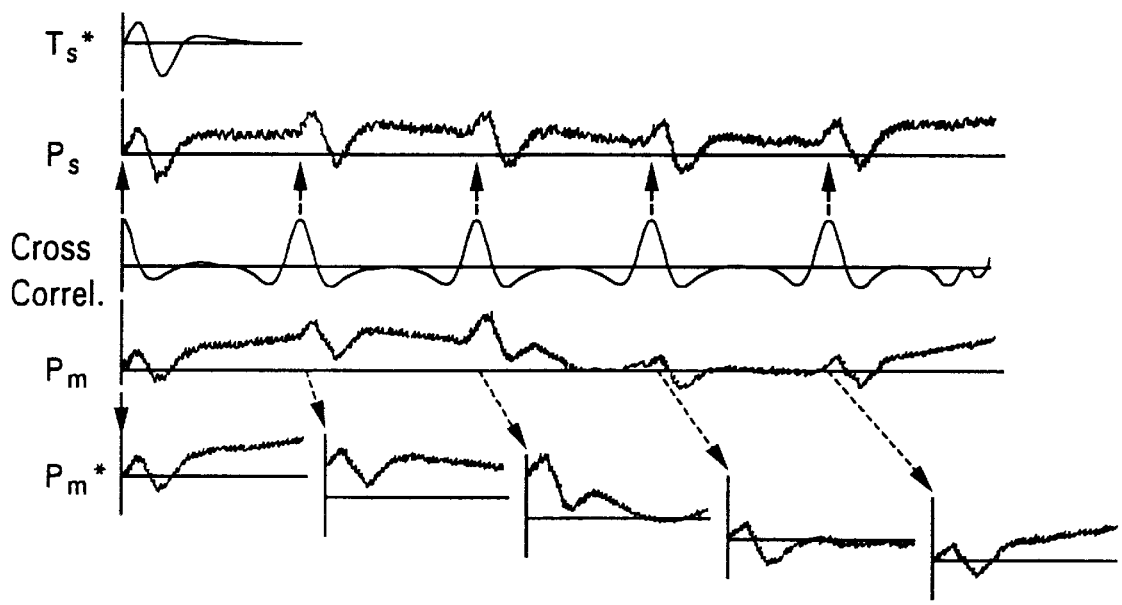
FIG. 8 is a schematic description of the data sampling and processing techniques employed according to the preferred embodiment of the present invention.

FIG. 8 is a schematic description of the data sampling and processing techniques employed according to the preferred embodiment of the present invention. As is shown, a template signal $T_s^*$ is calculated from a sample of 200 measurements of supply pressure $P_s$ (measured by the pressure transducer at the supply of air or gas). This composite or average template is used as a benchmark for comparison of data to insure that a full cycle of the forced probing signal is represented in the data ensembles sampled and selected for analysis. Similar templates ($T_m^*$, $T_Q^*$) are calculated for mask pressure $P_m$ and flow rate $Q_t$.

The sampled pressure data $P_s$ is cross-correlated with the template signal $T_s^*$ using local maxima in the cross-correlation signal to identify 256 data points corresponding to one cycle of the forced probing signal. The 256 data points identified by the cross-correlation identify a corresponding 256 data points in the mask pressure signal $P_m$ (pressure measured by the pressure transducer in the mask). Thus, selected 256-point data ensembles of the mask pressure $P_m^*$ representative of a full cycle of the forced probing signal are obtained for use in the calculation of the airway obstruction index, as described above. Similar 256-point data ensembles for flow rate $Q_t$ are obtained by correspondence with the cross-correlated supply pressure $P_s$ signal. Correlation of the pressure supply $P_s$ signal is preferred because it maintains a relatively uniform periodicity.

Also, the template values $T_s^*$, $T_m^*$, $T_Q^*$ are updated with newly measured data according to the formula:

$$T_k(i) = T_{k-1}(i)*(1-\alpha) + \alpha*W(i) \tag{4}$$

Where T is the template in question ($T_s^*$, $T_m^*$, $T_Q^*$) W is the current selected segment or cycle of 256 data points ($P_s^*$, $P_m^*$, $Q_t^*$), i is an index from 1 to 256, and $\alpha$ is the updating rate of 0.02. Thus the current template ($T_k$) is comprised of 98% of the previous template ($T_{k-1}$) and 2% of new qualified and selected signal (W). This relationship can also be used to derive an initial and subsequent template value in lieu of creating a template from 200 previously measured values.

Figure 9:
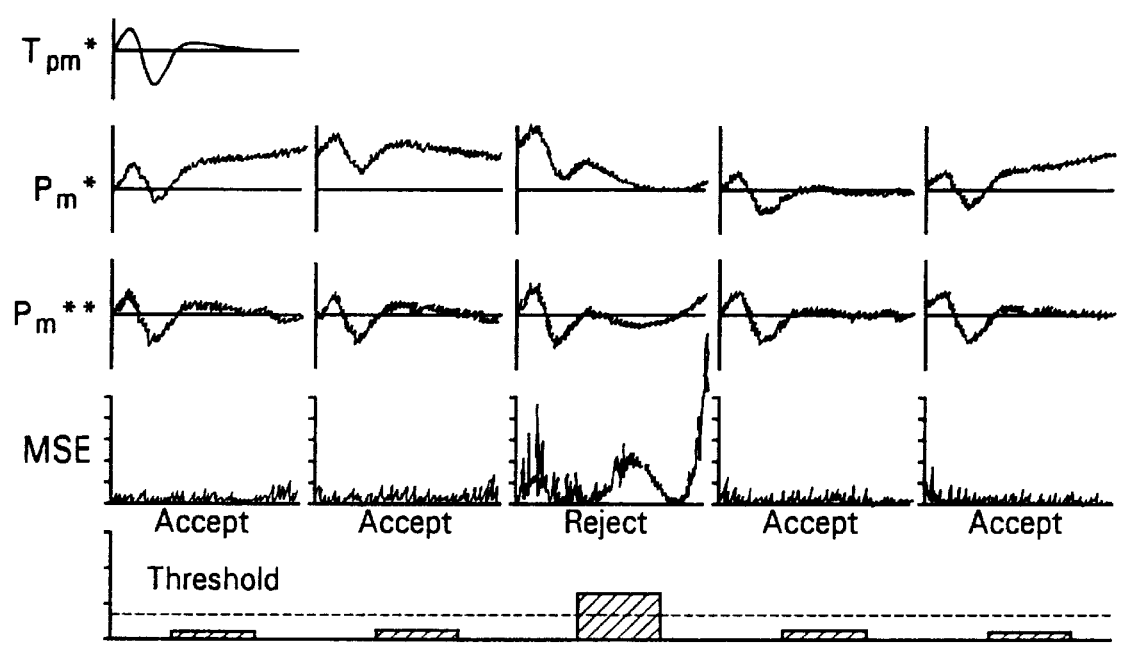
FIG. 9 is a graphic representation of the data processing that results in the discard of noisy or unreliable data according to the preferred embodiment of the present invention.

FIG. 9 is a graphic representation of the data processing that results in the discard of noisy or unreliable data. As a first step, each 256-point selected ensemble $P_m^*$ has its slope zeroed and intercept removed to provide a corrected ensemble $P_m^{}$. The mean squared error MSE between each corrected ensemble $P_m^{}$ and the template $T_m^*$ is calculated according to the following formula:

$$MSE = (T_m^* - P_m^{**})^2 \tag{5}$$

The MSE then is compared to a threshold value, which is selected to reject noisy signals and is based on an empirical study, and the ensemble $P_m^{**}$ is rejected if MSE exceeds the threshold.

Slope/Deviation Data Processing

The foregoing method of data processing for noisy or inaccurate data is relatively precise, but sacrifices computational resources and time. If a lower signal-to-noise ratio is present (such that it is futile to attempt to isolate data corresponding to a full cycle of the forced probing signal), a simpler, faster, but less accurate scheme may also be employed. According to this processing scheme, airflow data $Q_t$ is analyzed in 0.25 second intervals (again 256 data points at 1024 Hz). In this narrow time window, $Q_t$ resembles a straight line having a slope that increases or decreases depending on the presence of respiration. Data ($Q_t$ and corresponding ensembles of $P_m$) with a slope (positive or negative) exceeding a threshold is discarded as being influenced by respiration and likely to be inaccurate or unreliable.

Data not discarded after the slope test is discarded if its standard deviation exceeds twice the levels measured in the same quantities ($Q_t$ and $P_m$) during normal breathing. Standard deviation is a proxy for the rate of change of frequency of a given signal. If it is high, it indicates a noisy signal.

Coherence Function

As a final step, a coherence function employing the cross-power spectra of measured quantities is applied to the data not discarded after the either of the foregoing tests. The coherence function is obtained using the following formula:

$$\gamma^2 = \frac{|G_{QtPm}(\omega)|^2}{G_{PmPm}(\omega) G_{QtQt}(\omega)} \tag{6}$$

Where $\omega$ is the frequency, $G_{QtPm}$ the cross-power spectrum of airflow ($Q_t$) and mask pressure ($P_m$), $G_{PmPm}$ and $G_{QtQt}$ are cross-power spectra of the mask pressure ($P_m$) and the airflow ($Q_t$), respectively. The coherence function $\gamma^2$ reflects the "correlation" between the input and the output signals. The range of $\gamma^2$ is between 0.0 and 1.0. When $\gamma^2$ is equal to 1.0 at a certain frequency, it indicates a perfect linear, noise-free relation between pressure (input) and airflow (output) signals and the estimated respiratory impedance reflects the actual airway impedance at that frequency. Otherwise, the output signal is contaminated by noise that is not correlated to the input signal and the estimated respiratory impedance may be less reliable. According to the preferred embodiment of the present invention, data is discarded if it does not achieve a coherence of at least 0.85.

Regardless of the data processing and discard routine, valid data is then employed in equation (1) (or equation (2)), and an airway obstruction degree or impedance $Z_r$ is obtained for each frequency of interest (4, 8, 12, 16, and 20 Hz according to the preferred embodiment of the present invention and based on the 4 Hz forced probing signal). Each value of $Z_r$ is then averaged together according to the formula:

$$I_z = \frac{\sum Z_{r_n}}{n}$$

Where $Z_r$ is the respiratory impedance for a given frequency and n is the number of frequencies considered. According to the preferred embodiment of the present invention, $Z_r$ is determined for 4, 8, 12, 16, and 20 Hz and thus n is equal to five. Thus, an mean or average spectral value is obtained that may be used for diagnostic purposes. Moreover, the value may also be used in a therapeutic application for detection and treatement of sleep apnea in a therapeutic device based on change in the airway impedance or obstruction degree.

The method and apparatus according to the present invention provides some noteworthy advantages. The method can be performed on a sleeping patient without unduly restricting patient movement. The method may also be administered while the patient breathes and concurrently with the administration of pressurized gas for treatment of breathing disorders.

The invention has been described with reference to a preferred embodiment thereof. It is thus not limited, but is susceptible to variation and modification without departing from the scope and spirit of the invention.

We claim:

1. A method of determining the airway impedance of a patient comprising the steps of:
   supplying breathable gas to the patient's airways with an interface;
   applying a selected audio-frequency oscillation component to a pressure of the breathable gas;
   measuring pressure and flow of the breathable gas in the interface to obtain pressure and flow data characteristic of the patient's airway;
   converting the pressure and flow data to the frequency domain; and obtaining a mathematical function of the processed pressure and flow data to determine an index of airway impedance or degree of airway obstruction.

2. The method according to claim 1 further comprising processing the measured pressure and flow data to eliminate data having indicia of unreliability after converting it to the frequency domain.

3. The method according to claim 1 wherein the step of converting the measured pressure and flow data to the frequency domain further comprises the step of:

applying a Fourier transform to the measured pressure and flow data.

4. The method according to claim 1 wherein the oscillation is a multifrequency oscillation applied by a frequency generator and loudspeaker.

5. The method according to claim 1, wherein the step of obtaining the mathematical function comprises the steps of:

dividing the pressure data by the corresponding flow data to obtain an airway impedance or degree of airway obstruction value; and obtaining a mean impedance or degree of airway obstruction from the airway impedance or degree of airway obstruction values.

6. The method according to claim 2 wherein the processing step comprises:

discarding noisy pressure and flow data resulting from a blower supplying breathable gas to the patient's airways through the interface; and applying a coherence function to the pressure and flow data and discarding data with coherence less than a selected threshold.

7. A method of determining the airway impedance or degree of airway obstruction of a patient comprising the steps of:

supplying breathable gas to the patient's airways with an interface;

applying a selected audio-frequency oscillation component to a pressure of the breathable gas;

sampling pressure and flow of the breathable gas in the interface to obtain pressure and flow data characteristic of the patient's airway;

converting the sampled pressure and flow data to the frequency domain;

processing the converted pressure and flow data to eliminate data having indicia of unreliability; and obtaining a mathematical function of the processed pressure and flow data to determine an index of airway impedance or degree of airway obstruction.

8. The method according to claim 7 wherein the step of converting the measured pressure and flow data to the frequency domain further comprises the step of:

applying a Fourier transform to the sampled pressure and flow data prior to, processing the pressure and flow data.

9. The method according to claim 7 wherein the oscillation is a multifrequency oscillation applied by a frequency generator and loudspeaker.

10. The method according to claim 7, wherein the step of obtaining the mathematical function comprises the steps of:

dividing processed pressure data by corresponding processed flow data to obtain an airway impedance or degree of airway obstruction value; and obtaining a mean impedance or degree of airway obstruction from the airway impedance or degree of airway obstruction values.

11. The method according to claim 7 wherein the processing step comprises:

discarding noisy pressure and flow data resulting from a blower supplying breathable gas to the patient's airways through the interface; and applying a coherence function to the pressure and flow data and discarding data with coherence less than a selected threshold.

12. A method of determining the airway impedance or degree of airway obstruction of a patient comprising the steps of:

supplying breathable gas to the patient's airways with an interface;

applying a selected audio frequency oscillation component of a selected frequency to the breathable gas;

measuring pressure and flow of the breathable gas in the interface to obtain pressure and flow data characteristic of the patient's airway;

converting the pressure and flow data to the frequency domain;

discarding converted pressure and flow data that have indicia of inaccuracy; and dividing the pressure data by the corresponding flow data to obtain an airway impedance or degree of airway obstruction value; and obtaining a mean impedance or degree of airway obstruction from the airway impedance or degree of airway obstruction values.

13. The method according to claim 12 wherein the step of converting the measured pressure and flow data to the frequency domain further comprises the step of:

applying a Fourier transform to the measured pressure and flow data prior to processing the pressure and flow data.

14. The method according to claim 12 wherein the oscillation is a multifrequency oscillation applied by a frequency generator and loudspeaker.

15. The method according to claim 12 wherein the discarding step comprises:

discarding noisy pressure and flow data resulting from a blower supplying breathable gas to the patients airways through the interface; and applying a coherence function to the pressure and flow data and discarding data with coherence less than a selected threshold.

16. An apparatus for determining the airway impedance or degree of airway obstruction of a patient comprising:

an interface adapted to be coupled to the patient's airways to supply a breathable gas;

means for applying a selected audio-frequency oscillation component to a pressure of the breathable gas;

at least one sensor in the interface to measure pressure and flow of the breathable gas in the interface and obtain pressure and flow data characteristic of the patient's airway; and a processor coupled to the sensor to convert the pressure and flow data to the frequency domain and to obtain a mathematical function of the processed pressure and flow data to determine an index of airway impedance or degree of airway obstruction.

* * * * *